(12) United States Patent
Mohapatra et al.

(10) Patent No.: US 7,892,553 B2
(45) Date of Patent: Feb. 22, 2011

(54) MATERIALS AND METHODS TO REDUCE LOW DENSITY LIPOPROTEIN CHOLESTEROL

(75) Inventors: Shyam S. Mohapatra, Lutz, FL (US); Arun Kumar, Tampa, FL (US)

(73) Assignee: University of South Florida, Tampa, FL (US)

( * ) Notice: Subject to any disclaimer, the term of this patent is extended or adjusted under 35 U.S.C. 154(b) by 595 days.

(21) Appl. No.: 11/799,367

(22) Filed: Apr. 30, 2007

(65) Prior Publication Data

US 2008/0075731 A1 Mar. 27, 2008

Related U.S. Application Data

(60) Provisional application No. 60/796,346, filed on Apr. 28, 2006.

(51) Int. Cl.
*A61K 39/395* (2006.01)
*B82B 3/00* (2006.01)

(52) U.S. Cl. .................. 424/172.1; 977/739; 977/746; 977/747; 977/900

(58) Field of Classification Search .............. 424/172.1; 977/900, 739, 746, 747
See application file for complete search history.

(56) References Cited

U.S. PATENT DOCUMENTS

| | | | | |
|---|---|---|---|---|
| 6,294,376 | B1 * | 9/2001 | Overturf et al. | 435/320.1 |
| 2004/0086885 | A1 * | 5/2004 | Lee et al. | 435/6 |
| 2006/0024231 | A1 * | 2/2006 | Schnitzer et al. | 424/1.49 |
| 2006/0078624 | A1 * | 4/2006 | Zalipsky et al. | 424/489 |
| 2007/0104649 | A1 * | 5/2007 | Fischer et al. | 424/9.6 |

OTHER PUBLICATIONS

Traverso, M. 2004. How the reducing agents (NADH and FADH2) able to generate the free-energy currency . . . , Washington University in St Louis, © 2004, 3 pages.*
Garg, R. et al. "Non-high density lipoprotein cholesterol: Why lower is better" *Preventative Cardiology*, 2005, pp. 173-177, vol. 8, No. 3; abstract.
Gylling, H. et al. *Curr Opin Investig Drugs.*, Mar. 2006, pp. 214-218, vol. 7, No. 3; abstract.
Hernando, A. et al. *Scientific World Journal*, 2005, pp. 972-1001, vol. 5; abstract.
Jones, K.B. *Jr Int Surg.*, 2004, pp. 51-57, vol. 89, No. 1; abstract.
Lee, H.Y. et al. *J Nanosci Nanotechnol*, 2002, pp. 613-615, vol. 2, No. 6; abstract.
Pouliquen, D. et al. *Magn Reson Imaging*, 1993, pp. 219-228, vol. 11, No. 2; abstract.
Rodenburg, J. et al. *Pediatr Endocrinol Rev.*, 2004, pp. 171-180, vol. 2(Suppl 1); abstract.
Stone, N.J. *Endocrinal Metab Clin North Am.*, 1990, pp. 321-344, vol. 19, No. 2; abstract.
Alexiou, C. et al. "Targeting Cancer Cells: Magnetic Nanoparticles as Drug Carriers" *Eur Biophys J.*, Jan. 31, 2006, pp. 446-450, vol. 35.
Almhanna, K. et al. "Sideroblastic Anemia After Bariatric Surgery" *Am J Hematol.*, 2006, pp. 155-156, vol. 81, No. 2.
Bruckl, H. et al. "Magnetic Particles as Markers and Carriers of Biomolecules" *IEE Proc Nanobiotechnol.*, Feb. 2005, pp. 41-46, vol. 152, No. 1.
Chapman, M.J. et al. "The Potential Role of HDL- and LDL-Cholesterol Modulation in Atheromatous Plaque Development" *Curr Med Res Opin.*, 2005, pp. S17-S22, vol. 21 (Suppl 6).
Chiang, J.Y.L. et al. "Regulation of Cholesterol 7α-Hydroxylase in the Liver" *J. Biol. Chem.*, 1990, pp. 3889-3897, vol. 265, No. 7.
Choi, H. et al. "Iron Oxide Nanoparticles as Magnetic Resonance Contrast Agent for Tumor Imaging via Folate Receptor-targeted Delivery" *Acad. Radiol.*, 2004, pp. 996-1004, vol. 11, No. 9.
Chu, Y. et al. "Growth and Characterization of Highly Branched Nanostructures of Magnetic Nanoparticles" *J Phys Chem B Condens Matter Mater Surf Interfaces Biophys.*, Feb. 23, 2006, pp. 3135-3139, vol. 110, No. 7.
Dale, K.M. et al. "Statins and Cancer Risk: A Meta-Analysis" *JAMA*, Jan. 4, 2006, pp. 74-80, vol. 295, No. 1.
Daetwiler, S. "Intractable Abdominal Pain Following Laparoscopic Adjustable Gastric Banding" *Obes Surg.*, 2005, pp. 1341-1343, vol. 15, No. 9.
Dixit, V. et al. "Synthesis and Grafting of Thioctic Acid—PEG—Folate Conjugates onto Au Nanoparticles for Selective Targeting of Folate Receptor—Positive Tumor Cells" *Bioconjug. Chem.*, 2006, pp. 603-609, vol. 17, No. 3.
Fuentes, M. et al. "Preparation of Inert Magnetic Nano-Particles for the Directed Immobilization of Antibodies" *Biosens Bioelectron*, 2005 pp. 1380-1387, vol. 20, No. 7.

(Continued)

*Primary Examiner*—Jon P Weber
*Assistant Examiner*—Kailash C Srivastava
(74) *Attorney, Agent, or Firm*—Saliwanchik, Lloyd & Saliwanchik

(57) ABSTRACT

The present invention pertains to nanoparticles, comprising a metal and/or polymer core, with 7-alpha hydroxylase, or an enzymatically active fragment thereof, nicotinamide adenine dinucleotide (NADH) and antibodies, or antibody fragments, specific for low density lipoprotein (LDL), attached to the core. The invention also concerns methods for reducing LDL cholesterol in a human or animal subject by administering nanoparticles of the invention. In a preferred embodiment, both circulating LDL and plasma cholesterol levels are reduced in the subject.

10 Claims, 11 Drawing Sheets

OTHER PUBLICATIONS

Gomez-Lopera, S.A. et al. "Colloidal Stability of Magnetite /Poly (lactic acid) Core/Shell Nanoparticles" *Langmuir*, 2006, pp. 2816-2821, vol. 22, No. 6.

Gotto, A.M. Jr. "Structural Mechanism for Statin Inhibition of 3-hydroxy-3-methylglutaryl Coenzyme A reductase" *Am Heart J.*, 2002, pp. S33-S42, vol. 144, No. 6.

Gu, H. "Biofunctional Magnetic Nanoparticles for protein separation and pathogen detection" *Chem Commun (Camb).*, Mar. 7, 2006, pp. 941-949, vol. 9.

Jacobs, E.J. et al. "Cholesterol-Lowering Drugs and Colorectal Cancer Incidence in a Large United States Cohort" *J Natl Cancer Inst.*, 2006, pp. 69-72, vol. 98, No. 1.

Kim, S.H. et al. "Target-Specific Cellular Uptake of PLGA Nanoparticles Coated with Poly(L-lysine)—Poly( ethylene glycol)—Folate Conjugate" *Langmuir*, 2005, pp. 8852-8857, vol. 21, No. 19.

Koh, I. et al. "Magnetic Iron Oxide Nanoparticles for Biorecognition: Evaluation of Surface Coverage and Activity" *J Phys Chem BCondens Matter Mater Surf Interfaces Biophys.*, Feb. 2, 2006, pp. 1553-1558, vol. 110, No. 4.

Kohler, N. et al. "A Bifunctional Poly(ethylene glycol) Silane Immobilized on Metallic Oxide-Based Nanoparticles for Conjugation with Cell Targeting Agents" *J. Am. Chem. Soc.*, 2004, pp. 7206-7211, vol. 126, No. 23.

Kohler, N. et al. "Methotrexate-Immobilized Poly(ethylene glycol) Magnetic Nanoparticles for MR Imaging and Drug Delivery" *Small*, 2006, pp. 785-792, vol. 2, No. 6.

Korenkov, M. et al. "Surgery for Obesity" *Curr Opin Gastroenterol.*, 2005, pp. 679-683, vol. 21, No. 6.

Kuhn, S.J. et al. "Characterization of Superparamagnetic Nanoparticle Interactions with Extracellular Matrix in an in Vitro System" *Ann Biomed Eng.*, Jan. 2006, pp. 51-58, vol. 34, No. 1, Epub Feb. 14, 2006.

Li, T. et al. "Bile Acids and Citokines Inhibit the Human Cholesterol 7α-Hydroxylase Gene via the JNK/c-Jun Pathway in Human Liver Cells" *Hepatology*, 2006, pp. 1202-1210, vol. 43, No. 6.

Loewe, C. "LAP-Banding Obesity: A Case of Stomach Perforation, Peritonitis, and Death" *Am J Forensic Med Pathol,.* 2005, pp. 297-330, vol. 26, No. 3.

Matheson, H.B. et al. "Cholesterol 7α-Hydroxylase Activity is Increased by Dietary Modification with Psyllium Hydrocolloid, Pectin, Cholesterol and Cholestyramine in Rats [1,2,3]" *J. Nutr.*, 1995, pp. 454-458, vol. 125, No. 3.

Miller, J.P. et al. "Triglyceride Lowering Effect of MaxEPA Fish Lipid Concentrate: A Multicentre Placebo Controlled Double Blind Study" *Clin Chim Acta.*, 1988, pp. 251-259, vol. 178, No. 3.

Osaka, T. et al. "Synthesis of Magnetic Nanoparticles and Their Application to Bioassays" *Anal Bioanal Chem.*, Feb. 2006, pp. 593-600, vol. 384, No. 3, Epub Jan. 4, 2006.

Schmitz, G. et al. "Pharmacogenomics and Pharmacogenetics of Cholesterol-Lowering Therapy" *Clin Chem Lab Med.*, 2003, pp. 581-589, vol. 41, No. 4.

Schmitz, G. et al. "Pharmacogenomics of Cholesterol-Lowering Therapy" *T Vascul Pharmacol.*, 2006, pp. 75-89, vol. 44, No. 2.

Shang, H. et al. "Synthesis and Characterization of Paramagnetic Microparticles Through Emulsion-Templated Free Radical Polymerization" *Langmuir.*, Mar. 14, 2006, pp. 2516-2522, vol. 22, No. 6.

Sirtori, C.R. et al. "LDL-Cholesterol lowering or HDL-Cholesterol Raising for Cardiovascular Prevention: A Lesson from Cholesterol Turnover Studies and Others" *Atherosclerosis*, May 2006, pp. 1-11, vol. 186, No. 1, Epub Nov. 28, 2005.

Stroes, E. et al. "Statins and LDL-Cholesterol Lowering: An Overview" *Curr Med Res Opin.*, 2005, pp. S9-S16, vol. 21 (Suppl 6).

Sun, C. et al. "Folic Acid-PEG Conjugated Superparamagnetic Nanoparticles for Targeted Cellular Uptake and Detection by MRI" *J. Biomed. Mater. Res. A.*, 2006, pp. 550-557, vol. 78, No. 3.

Thorek, D.L. et al. "Superparamagnetic Iron Oxide Nanoparticle Probes for Molecular Imaging" *Ann Biomed Eng.*, Jan. 2006, pp. 23-28, vol. 34, No. 1.

Thunemann, A.F. et al. "Maghemite Nanoparticles Protectively Coated with Poly(ethylene imine) and Poly(ethylene oxide)-*block*-Poly(glutamic acid)" *Langmuir*, Feb. 28, 2006, pp. 2351-2357, vol. 22, No. 5.

Van Cantfort, J. et al. "Rat Liver Cholesterol 7α-Hydroxylase" *Eur. J. Biochem.*, 1975, pp. 23-31, vol. 55, No. 1.

Wang, D.P. et al. "Short Communication: Structure and Nucleotide Sequences of the Human Cholesterol 7α-Hydroxylase Gene (CYP7)" *Genomics*, 1994, pp. 320-323, vol. 20, No. 2.

Wang, J. et al. "Linkage Between Cholesterol 7α-Hydroxylase and High Plasma Low-Density Lipoprotein Cholesterol Concentrations" *J. Clin. Invest.*, 1998, pp. 1283-1291, vol. 101, No. 6.

Willner, I. et al. "Controlling Chemical Reactivity at Solid-Solution Interfaces by Means of Hydrophobic Magnetic Nanoparticles" *Langmuir*, Feb. 14, 2006, pp. 1409-1419, vol. 22, No. 4.

Winocour, P.H. "Drug Therapy for Prevention of Cardiovascular Disease—Should Surrogate Measures be Abandoned?" *Clin Med.*, 2005, pp. 282-286, vol. 5, No. 3, Review.

\* cited by examiner

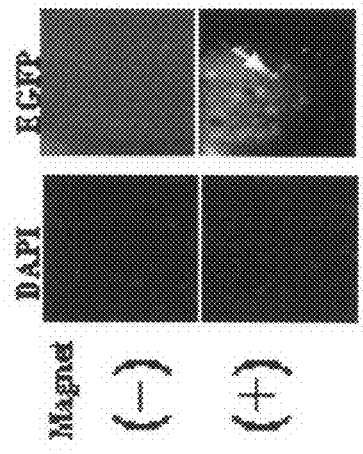
FIG. 6A
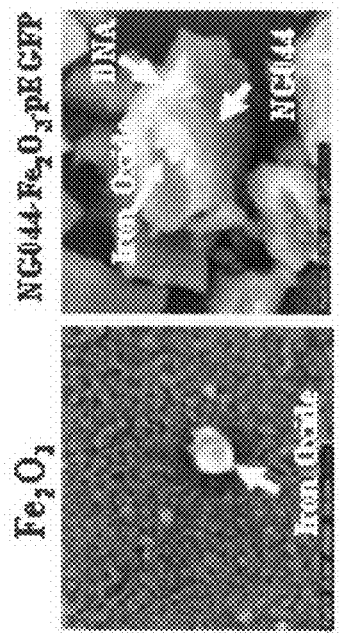
FIG. 6B
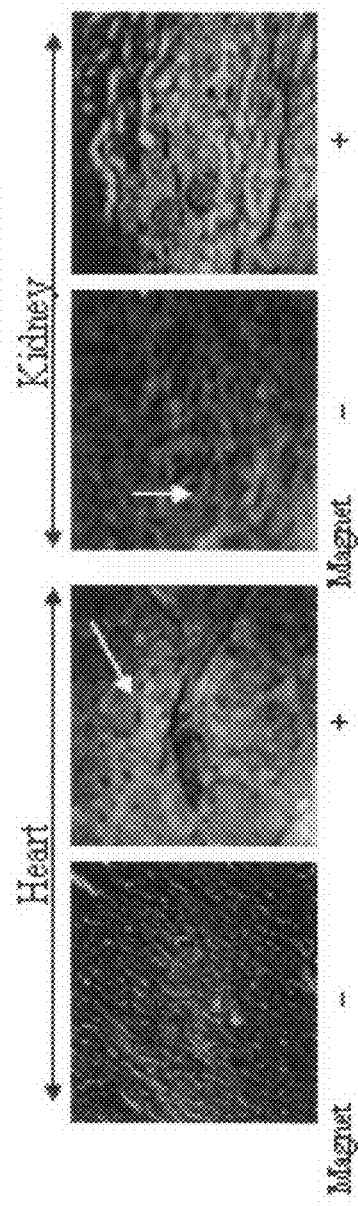
FIG. 6C
FIG. 6D

MATERIALS AND METHODS TO REDUCE LOW DENSITY LIPOPROTEIN CHOLESTEROL

CROSS-REFERENCE TO RELATED APPLICATION

The present application claims the benefit of U.S. Provisional Application Ser. No. 60/796,346, filed Apr. 28, 2006, which is hereby incorporated by reference herein in its entirety, including any figures, tables, nucleic acid sequences, amino acid sequences, and drawings.

BACKGROUND OF THE INVENTION

Cholesterol is an extremely important molecule in the body. It is a key component of cell membranes and is utilized in the formation of steroid hormones and bile acids. Because of its insolubility, it does not travel freely in the bloodstream but is carried by particles called lipoproteins. There are several different types of lipoprotein and the fate of cholesterol is different depending on which type of lipoprotein carries it. Low density lipoproteins (LDL) can deposit excess cholesterol on the arterial linings while high density lipoprotein (HDL) can remove excess cholesterol from peripheral tissues and transport it to the liver for excretion. LDL, the major carrier of plasma cholesterol, is taken up by the liver and peripheral cells, largely via receptors that recognize apoprotein B. The cytoplasmic pool of cholesterol is derived partly from LDL and partly by endogenous biosynthesis (Chapman, M J et al. *Curr Med Res Opin.,* 2005, 21(Suppl 6):S17-22).

Regulation of plasma cholesterol levels has to be tightly controlled in order to insure adequate supplies for the cells but not so much as to result in cholesterol deposition and atherosclerosis. Excretion of bile salts is the major route for regulating cholesterol levels. In the liver, excess cholesterol is converted to bile acids which, after secretion in the bile, are ultimately excreted in the feces. There is an additional pathway for lowering plasma cholesterol levels and that is called reverse cholesterol transport. This process is mediated by HDL which is able to absorb cholesterol from peripheral tissues and from arterial wall macrophages and carry it to the liver for conversion to bile acids and excretion.

Lowering cholesterol is important for everyone, including younger, middle-aged, and older adults, and people with or without heart disease and/or stroke. Lowering high cholesterol levels lessens the risk for developing heart disease and reduces the chance of a heart attack or dying of heart disease (Stone, N J, *Endocrinol Metab Clin North Am.,* 1990, 19(2):321-44); Chapman, M J *Curr Med Res Opin.,* 2005, 21(Suppl 6):S17-22).

In accordance with the National Heart, Lung, and Blood Institute's Cholesterol Education Program (NCEP), everyone age 20 and older should have their cholesterol and triglyceride levels measured at least once every five years. HDL cholesterol protects against heart disease. This means that higher numbers of HDL cholesterol are better. A level less than 40 mg/dL is considered low and a major risk factor for the development of coronary artery disease. HDL levels of 60 mg/dL or more help to lower your risk for heart disease. Triglycerides also can raise heart disease risk. Levels that are borderline high (150-199 mg/dL) or high (200 mg/dL or more) may require treatment for some people. The NHLBI classification of the optimal level of LDL cholesterol is less than 100 mg/dL. Borderline high LDL cholesterol is 130-159 mg/dL, and very high is 190 mg/dL and above. High LDL cholesterol always requires attention. One's chance of developing coronary artery disease increases with the presence of one or more heart disease risk factors, such as high blood pressure, diabetes, and/or an early family history of heart disease. It is estimated that 7 million American adults have high cholesterol. While other factors such as high blood pressure, diabetes, smoking, or a family history, contribute to high cholesterol, more than half of all heart disease is associated with lipid abnormalities. Decreasing total cholesterol by 10% can result in a 30% reduction in coronary heart disease incidence.

This is especially true for people who have already suffered a heart attack. If plaques have narrowed the arteries around the heart and restricted the flow of oxygen-rich blood to the heart's muscles it may cause coronary artery disease. There are several ways to treat high cholesterol, such as by switching to a cholesterol-lowering diet (called the TLC diet), increasing physical activity, and reducing obesity. When the LDL level is greater than 160 mg/dL, it may be necessary to take cholesterol-lowering drugs together with TLC treatment to lower LDL cholesterol levels sufficiently.

Medications that reduce blood cholesterol levels include, but are not limited to, (a) cholesterol sequestration drugs; (b) triglyceride-lowering drugs; and (c) cholesterol pathway blockers (statins). Cholesterol sequestration drugs (resins), such as cholestyramine (Questran) and colestipol (Colestid), are used to lower cholesterol indirectly by binding with bile acids in the intestinal tract. The liver makes bile acids, which are needed for digestion, from cholesterol. By sequestering bile acids, resins induce the liver to make more bile acids, thus reducing the cholesterol in the bloodstream (Schmitz, G and Langmann, T *Vascul Pharmacol.,* 2006, 44(2):75-89; Schmitz, G et al. *Clin Chem Lab Med.,* 2003, 41(4):581-9). Triglyceride-lowering drugs include fibrates, such as gemfibrozil (Lopid) and fenofibrate (Tricor), and the vitamin niacin (nicotinic acid), which reduce triglyceride production and remove triglycerides from circulation. They can also increase HDL (Gotto, A M Jr. *Am Heart J.,* 2002, 144(6):S33-42; Miller, J P et al. *Clin Chim Acta.,* 1988, 178(3):251-9). Statins are competitive inhibitors of HMG-CoA reductase, the key enzyme in the cholesterol biosynthesis pathway. This depletes cholesterol in liver cells, which causes the liver cells to remove cholesterol from the blood (Rodenburg, J et al. *Pediatr Endocrinol Rev.,* 2004, 2(Suppl 1):171-80; Gylling, H et al. *Curr Opin Investig Drugs.,* 2006 March, 7(3):214-8). Statins can reduce LDL cholesterol by up to 40 percent. Statins may also help the body reabsorb cholesterol from plaques that accumulate on the walls of the arteries, thus making them less likely to cause complications such as a heart attack or stroke. Statins include fluvastatin (Lescol), lovastatin (Mevacor), simvastatin (Zocor), pravastatin (Pravachol) and atorvastatin (Lipitor) (Stroes, E et al. *Curr Med Res Opin.,* 2005, 21(Suppl 6):S9-16).

However, some people are unusually sensitive to the effects of some cholesterol-reducing drugs. For example, gemfibrozil may increase the risk of some types of cancer, and may cause gallstones or muscle problems. HMG-CoA reductase inhibitors (statins) may damage the liver or muscles (Dale, K M et al. *JAMA,* 2006 Jan. 4, 295(1):74-80). Cholesterol-reducing drugs may interact with other medicines—the effects of one or both of the drugs may change, thus interfering with the therapeutic effect, or the risk of side effects may be greater. None of these procedures can cure coronary heart disease (CHD). They open the vessels, improving blood flow and relieving symptoms, but lifestyle changes or medication will still be needed to halt the progress of the underlying disease (Jacobs, E J et al. *J Natl Cancer Inst.*, 2006, 98(1): 69-72; Rodenburg, J et al. *Pediatr Endocrinol Rev.*, 2004, 2(Suppl 1):171-80).

Surgical procedures for cholesterol reduction include gastric stapling performed on severely obese patients, during which the stomach walls are stapled together to create a smaller stomach pouch, thus reducing the volume of the stomach by vertical banded gastroplasty, video-assisted laparoscopy, or open-surgery methods (Almhanna, K et al. *Am J Hematol.*, 2006 February, 81(2):155-156; *Health News.*, 2005 July, 11(7):14). Also, bariatric surgery provides a significant improvement in cases of high cholesterol; however, it carries the usual pain and risks of any major gastrointestinal surgical operation and patients have a lifelong risk of nutritional deficiencies (Korenkov, M et al. *Curr Opin Gastroenterol.*, 2005, 21(6):679-83). Other cholesterol reducing measures include gastric bypass, which produces a feeling of stomach fullness, thereby decreasing food intake (Jones, K B Jr *Int Surg.*, 2004, 89(1):51-7) or gastroplasty which reroutes the digestive system, but it also restricts the amount of food that can be eaten by making the stomach smaller (Loewe, C, *Am J Forensic Med Pathol.*, 2005, 26(3):297-30). Potential side effects resulting from lap band and gastroplasty include "dumping syndrome" which is a combination of nausea, chest, and abdominal cramps, sweating, and diarrhea. Other risks and complications include malabsorption, vitamin deficiencies, and chronic abdominal pain (Daetwiler, S *Obes Surg.*, 2005, 15(9):1341-3; Almhanna, K et al. *Am J Hematol.*, 2006 February, 81(2):155-156; Srikanth, M S *Obes Surg.*, 2005, 15(8):1165-70). In essence, the current cholesterol reduction procedures are far from optimal.

Although magnetic microparticles are already being successfully used in commercial DNA isolation, their unique properties offer distinct advantages, such as higher surface area, super-paramagnetism and tunable magnetic response, that can be used in biomedical applications such as organ/tissue targeted diagnosis and drug delivery, detoxification of biological fluids, magnetically controlled drug delivery, magnetic resonance imaging (MRI) contrast enhancement and magnetic cell separation (Thorek, D L et al. *Ann Biomed Eng.*, 2006 January, 34(1):23-38; Gu, H, *Chem Commun (Camb).*, 2006 Mar. 7, (9):941-9). In biomedical applications, the magnetic particles either form the core ($Fe_3O_4$ or $Fe_2O_3$), which is functionalized by surface modification with biocompatible polymers and ligands, or include biocompatible polymers coacervated with magnetic nanoparticles, as shown in the data described herein. Additional magnetic particles, containing iron, cobalt, nickel, aluminum or cobalt/silica, are under investigation. In essence, the magnetic particles can be considered active substrates for selective biochemical reactions. The process of polymerization not only provides effective encapsulation of individual nanoparticles but also controls the growth in size, thus yielding a better overall size distribution. It is important to study the magnetic properties of nanopowders comprising polymer-coated particles and, in particular, to determine the role of the polymer in controlling the magnetic interactions. It is likely that the polymer coating directly affects interparticle separation and thus alters the exchange interactions that are the basis for super-paramagnetic or ferromagnetic behavior (Alexiou, C et al. *Eur Biophys J.*, 2006 Jan. 31, 1-5).

BRIEF SUMMARY OF THE INVENTION

The present invention pertains to nanoparticles targeted to low-density lipoprotein (LDL) and a safe and effective reverse transport method utilizing the nanoparticles targeted to LDL. Preferably, this new process has the dual effect of reducing both circulating LDL and plasma cholesterol levels.

Thus, one aspect of the present invention pertains to a method to reverse the cholesterol selectively by targeting LDL with the nanoparticles of the invention. In a preferred embodiment, the administered nanoparticles reduce both circulating LDL and plasma cholesterol levels in a subject to which the nanoparticles are administered.

In another aspect, the invention includes a nanoparticle comprising a core comprising a metal and/or a polymer; and a low-density lipoprotein (LDL) binding agent, 7-alpha hydroxylase or an enzymatically active fragment thereof, and nicotinamide adenine dinucleotide (NADH) attached to the core. In one embodiment, the core comprises $Fe_3O_4$ and/or $Fe_2O_3$. In another embodiment, the core comprises at least one metal selected from the group consisting of iron, cobalt, nickel, aluminum, and cobalt/silica. In another embodiment, the core comprises a metal, chitosan (a biocompatible polymer), or both. Preferably, in each embodiment, the LDL binding agent is an antibody or antibody fragment that specifically binds to LDL. Optionally, the core further comprises a polymer coating, such as polyethylene glycol (PEG). Optionally, the nanoparticle further comprises a reporter molecule.

Advantageously, in those embodiments in which the core comprises a metal, the nanoparticles can be magnetically controlled and induced to accumulate at a target anatomical site within the subject, using a magnet.

Preferably, preparation of the magnetic nanoparticles is performed in an aqueous medium to obtain particles of a specific size. In the next step, LDL antibodies, 7-alpha hydroxylase and the enzyme cofactor NADH are adsorbed to the particles and the resulting LAMPs are tested in vitro. LAMPs are mixed with a blood serum sample, stirred, and the relative levels of LDL and HDL are determined spectrophotometrically. The LAMPs are able to specifically remove LDL from serum. For in vivo determinations, FITC-labeled magnetic particles are injected into mice and directed to the heart or kidney using a magnet. The organs expose to the magnetic field show significantly elevated levels of LAMPs.

In another aspect, the present invention includes a method of preparing the nanoparticles. In preparing homogeneous nanoparticles comprising iron, it is preferable to perform the reaction under basic aqueous conditions without surfactants using a molar ratio of Fe (II):Fe (III)=1:2. Deionized water (resistance 17.8 MΩ) can be used to suspend the components with vigorous stirring. The resulting aqueous suspension can be precipitated by the spray method and the resulting magnetic particles washed with deionized water to remove unreacted components (Garg, R et al. *Prev Cardiol.*, 2005, 8(3): 173-177, Review; Sirtori, C R and Fumagalli, R et al. *Atherosclerosis*, May 2006, 186(1):1-11, Epub Nov. 28, 2005).

To attach LDL antibodies and 7-alpha hydroxylase to the magnetic nanoparticles, a solution of LDL antibodies in deionized water is mixed with 0.5 mL of carbodiimide solution and added to a colloidal suspension of magnetic nanoparticles. The solution is left to stand for 15 minutes to allow hydrolysis of the surface groups and formation of vitreophilic nanoparticles. The functionalized suspension is stirred vigorously and allowed to stand for at least 24 hours to produce LDLAb-$Fe_2O_3$ (LAMP) nanoparticles. The same procedure is followed for adsorbing 7-alpha hydroxylase to the LAMPs (Rodenburg, J et al. *Pediatr Endocrinol Rev.*, 2004, 2(Suppl 1):171-180, Review; Winocour, P H *Clin Med.*, 2005, 5(3): 282-286, Review).

The LAMPs are then washed with deionized water to remove any excess components and added to a mixture of ethanol and NH$_4$OH (25%) with vigorous stirring. The suspension is then gently stirred for 2 hours at room temperature, and the water evaporated under vacuum. The average diameter of the LAMPs can be determined by transmission electron microscopy (TEM). The coupling of the antibodies and enzyme can be confirmed by Fourier transform infrared spectroscopy (FTIR). FTIR measurements showed that LAMPs specifically bind LDL in solutions containing both LDL and HDL (Shang, H et al. *Langmuir,* 2006 Mar. 14, 22(6):2516-2522; Gomez-Lopera, S A et al. *Langmuir,* 2006 Mar. 14, 22(6):2816-2821; Fuentes, M et al. *Biosens Bioelectron,* 2005, 20(7):1380-1387; Lee, H Y et al. *J Nanosci Nanotechnol,* 2002, 2(6):613-615; Chu, Y et al. *J Phys Chem B Condens Matter Mater Surf Interfaces Biophys.,* 2006 Feb. 23, 110(7):3135-3139; Hernando, A et al. *Scientific World Journal,* 2005, 5:972-1001, Review; Osaka, T et al. *Anal Bioanal Chem.,* 2006 February, 384(3):593-600, Epub Jan. 4, 2006; Pouliquen, D et al. *Magn Reson Imaging,* 1993, 11(2):219-228).

In one embodiment, the magnetic nanoparticle of the invention comprises a core of Fe$_3$O$_4$ or Fe$_2$O$_3$, and/or other materials such as iron, cobalt, nickel, aluminum, cobalt/silica, wherein the enzyme 7-alpha hydroxylase, enzyme cofactor NADH, and antibodies (or antibody fragments) that specifically bind LDL are attached to the core. Optionally, the nanoparticle core can be coated or encapsulated with a polymer, such as polyethylene glycol (PEG), or other biocompatible substance, which can serve to increase the half-life of the nanoparticle in blood.

In another aspect, the method of the present invention comprises administering an effective amount of nanoparticles of specific size coupled with LDL antibodies and hydroxylase enzyme with NADH and encapsulated with PEG or any other material that is biological compatible and can be used for in vivo application to a human or animal patient in need of such treatment. The present inventors have determined that introduction of modified nanoparticles into an in vitro system can reduce the LDL cholesterol specifically. In one embodiment, the core comprises PEG-coated iron oxide. In another embodiment, the core comprises PEG-coated chitosan. In those embodiments in which the core comprises chitosan, the LDL binding agent and other components may attach, for example, at chitosan amide groups or at other accessible points on the particles.

Optionally, the nanoparticles of the invention can include a reporter molecule useful for tracking the location of the nanoparticles within a subject. A variety of different types of substances can serve as the reporter molecule, including but not limited to enzymes, dyes, radioactive metal and non-metal isotopes, fluorogenic compounds, fluorescent compounds, etc. For example, green fluorescent protein (GFP) or nucleic acids encoding GFP, or radioactive tags (such as [111]idium) can be used.

BRIEF DESCRIPTION OF THE DRAWINGS

FIGS. 6A-6D demonstrate external magnet-controlled targeting of nanoparticles. The Fe$_2$O$_3$ magnetic nanoparticles were prepared and incubated with pEGFP DNA, and the mixture was then complexed with Nanogene-044 (NG044). FIG. 6A shows the SEM pictures of Fe$_2$O$_3$ alone (left) or in complex with DNA and Nanogene-044 (NG044) (right). Different components are shown by arrowheads. Groups of BALB/c mice (n=4) were given the magnetic nanoparticles carrying 10 µg of pEGFP DNA by intravenous injection and a subgroup of mice had magnets placed close to the thoracic cavity for about 6 hours. Mice were sacrificed after 12 hours and were lavaged to detect EGFP positive cells in the BAL cells. Mice given plain NG044 particles without Fe$_2$O$_3$ were used as control. Results are shown in FIG. 6B. Heart tissue was fixed and embedded from mice exposed to magnet close to the thoracic cavity and the sections were visualized for EGFP positive (green) cells. Mice given plain NG044 particles without Fe$_2$O$_3$ were used as a control. Results are shown in FIG. 6C. Kidney tissue was fixed and embedded from mice exposed to magnet close to the kidney and the sections were visualized for EGFP positive (green) cells. Mice given plain NG044 particles without Fe$_2$O$_3$ were used as a control. Results are shown in FIG. 6D. Thus, external magnets can direct nanoparticles to specific organs or sites.

FIG. 7A shows a TEM of chitosan nanoparticles. The nanoparticles have a uniform size in the range of 60-80 nM. FIG. 7B shows a TEM of chitosan nanoparticles modified with LDL antibodies and 7-alpha hydroxylase.

DETAILED DISCLOSURE OF THE INVENTION

Figure 1A:
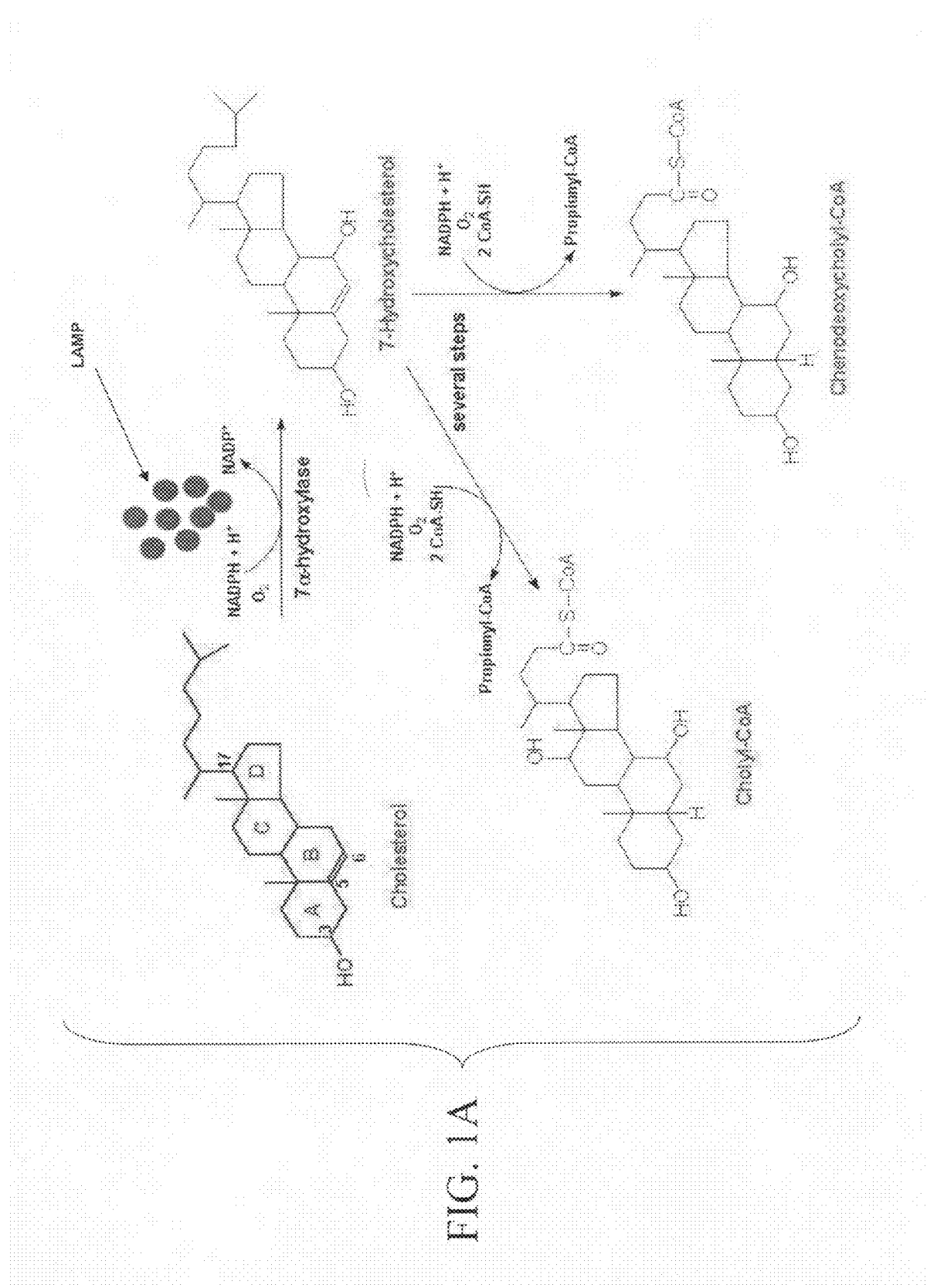
FIGS. 1A-1C are schematic diagrams depicting removal of cholesterol deposited in arteries or in other parts of the body using LAMP.
Figure 1B:
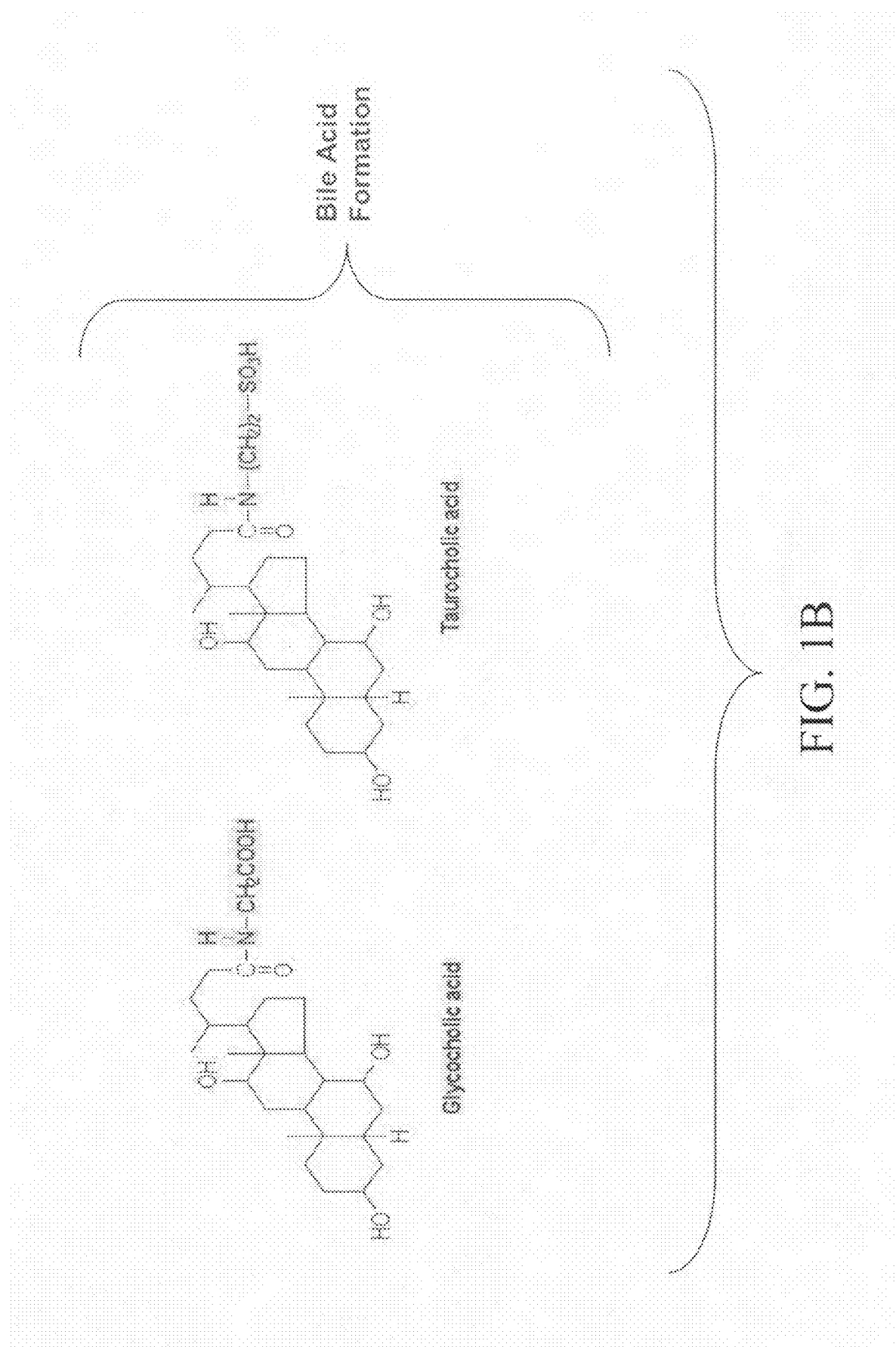

The present invention includes, but is not limited to, the following embodiments:

Embodiment 1: a method for reducing cholesterol, or for treating elevated cholesterol, including high cholesterol disease, comprising administering an effective amount of LDL-antibody coupled nanoparticles or LDL antibody-coupled magnetic nanoparticles (LAMP) to a human or non-human subject in need thereof.

Embodiment 2: the method of embodiment 1, wherein the step of administering comprises administering the nanoparticles to the subject, wherein the nanoparticles comprise low density lipoprotein antibodies, 7 hydroxylase enzyme, and NADH, or a biologically active fragment or homolog of any of the foregoing.

Embodiment 3: the method of embodiment 1, wherein the nanoparticles are LAMP and the LAMP comprise low density lipoprotein antibodies or enzyme or biocatalyst or a biologically active fragment or homolog of any of the foregoing.

Embodiment 4: the method of any one of embodiments 1 to 3, wherein the nanoparticles are administered to the subject by a route selected from the group consisting of oral, intramuscular, parenteral, intravenous, and intranasal.

Embodiment 5: the method of any one of embodiments 1 to 4, wherein the nanoparticles are administered with a pharmaceutically acceptable carrier.

Embodiment 6: the method of any one of embodiments 1 to 5, wherein the administering step comprises administering an expression vector containing and/or encoding one or more nanoparticle components (e.g., LDL binding agent, 7 alpha hydroxylase enzyme, and/or NADH).

Embodiment 7: the method of any one of embodiments 1 to 6, wherein the nanoparticles comprise chitosan and/or another biocompatible material, such as polyethylene glycol (PEG).

Embodiment 8: the method of any one of embodiments 1 to 7, wherein the nanoparticles cause a reduction of low density lipoprotein in the subject.

Embodiment 9: the method of any one of embodiments 1 to 8, wherein the nanoparticles inhibit (e.g., reduces the rate of or eliminates) further increase in the level of low density lipoprotein in the subject.

Embodiment 10: the method of any one of embodiments 1 to 9, wherein the subject is human or a non-human mammal.

Embodiment 11: the method of any one of embodiments 1 to 10, wherein the subject is suffering from a high level of cholesterol or a high level of low density lipoprotein.

Embodiment 12: a pharmaceutical composition comprising nanoparticles of the invention, such as LAMP, and a pharmaceutically acceptable carrier.

Embodiment 13: the pharmaceutical composition of embodiment 12, wherein the composition comprises nanoparticles with antibodies or antibody fragments that specifically bind to low density lipoprotein or a biologically active fragment or homolog thereof.

Embodiment 14: the pharmaceutical composition of embodiment 13, wherein the nanoparticles have antibodies to LDL or a biologically active fragment or homolog thereof.

Embodiment 15: the pharmaceutical composition of any one of embodiments 12 to 14, wherein the composition is a food, beverage, implant, endovascular prosthetic or another item that can be used for administration of the nanoparticles to a subject.

Embodiment 16: the pharmaceutical composition of any one of embodiments 12 to 15, wherein the composition is an intranasal spray, drops, gels, or powder.

As indicated above, the core of the nanoparticle can comprise a polymer, a metal, or both. Preferably, the polymer is a biocompatible polymer such as chitosan. Optionally, the nanoparticle core can be coated or encapsulated with a polymer, such as polyethylene glycol (PEG), which can serve to increase the half-life of the nanoparticle in blood. Preferably, the polymer has reactive groups that remain free as an attachment point for LDL binding agents or other targeting molecules (see, for example Sun C. et al., *J. Biomed. Mater. Res. A.*, 2006, 78(3):550-557; Choi H. et al., *Acad. Radiol.*, 2004, 11(9):996-1004; Kohler N. et al., *Small*, 2006, 2(6):785-792; Kohler N. et al., *J. Am. Chem. Soc.*, 2004, 126(23):7206-7211; Dixit V. et al., *Bioconjug. Chem.*, 2006, 17(3):603-609; and Kim S. H. et al., *Langmuir*, 2005, 21(19):8852-8857), which are each incorporated herein by reference in their entirety).

Optionally, the nanoparticles of the invention include a reporter molecule useful for tracking the location of the nanoparticles within a subject. For example, green fluorescent protein (GFP) or nucleic acids encoding GFP, or radioactive tags (such as $^{111}$idium) can be used.

At least one LDL binding agent, 7-alpha hydroxylase (CYP7) or an enzymatically active fragment thereof, and the coenzyme nicotinamide adenine dinucleotide (NADH, the reduced form of NAD$^+$) are also attached to the core. Preferably, the 7-alpha hydroxylase is the human enzyme or an enzymatically active fragment thereof (Wang D. P. and Chiang J. Y., *Genomics*, 1994, 20(2):320-323; U.S. Pat. No. 6,294,376, which are each incorporated herein by reference in their entirety). The enzymatic activity possessed by the enzyme (and its fragments) is known in the art, as are assays for the activity using liver microsomes, for example (Matheson H. B. et al., *J. Nutr.*, 1995, 125(3):454-458; Van Cantford J. et al., *Eur. J. Biochem.*, 1975, 55(1):23-31; Chiang J. Y. L. et al., *J. Biol. Chem.*, 1990, 265:3889-3897; Tiangang L. et al., *Hepatology*, 2006, 43(6):1202-1210; Wang J. et al., *J. Clin. Invest.*, 1998, 101(6):1283-1291, which are each incorporated herein by reference in their entirety).

LDL Binding Agents

Agents that are capable of binding LDL are those that interact or bind with at least a portion of the low-density lipoprotein. Examples of such agents (also referred to herein as binding agents) include, but are not limited to, antibodies (anti-LDL antibodies) or fragments thereof (such as Fab or (Fab)$_2$ fragments) that bind the lipoprotein, aptamers, and binding partners of the lipoprotein. Optionally, the binding agent is labeled with a detectable substance (e.g., a detectable moiety).

Antibodies specific for LDL that are used with the nanoparticles, compositions, and methods of the invention may be obtained from scientific or commercial sources. Alternatively, the isolated native lipoproteins or recombinant lipoproteins may be utilized to prepare antibodies, monoclonal or polyclonal antibodies, and immunologically active fragments (e.g., a Fab or (Fab)$_2$ fragment), an antibody heavy chain, an antibody light chain, humanized antibodies, a genetically engineered single chain F$_v$ molecule (Ladne et al., U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art. Preferably, antibodies used in the methods of the invention are reactive against LDL if they bind with a K$_a$ of greater than or equal to 10$^7$ M.

In order to produce monoclonal antibodies, a host mammal is inoculated with a lipoprotein representing the target LDL and then boosted. Spleens are collected from inoculated mammals a few days after the final boost. Cell suspensions from the spleens are fused with a tumor cell in accordance with the general method described by Kohler and Milstein (*Nature*, 1975, 256:495-497). In order to be useful, a peptide fragment must contain sufficient amino acid residues to define the epitope of the lipoprotein to be targeted.

If the fragment is too short to be immunogenic, it may be conjugated to a carrier molecule. Some suitable carrier molecules include keyhole limpet hemocyanin and bovine serum albumin. Conjugation may be carried out by methods known in the art. One such method is to combine a cysteine residue of the fragment with a cysteine residue on the carrier molecule. The peptide fragments may be synthesized by methods known in the art. Some suitable methods are described by Stuart and Young in "Solid Phase Peptide Synthesis," Second Edition, Pierce Chemical Company (1984).

Purification of the antibodies or fragments can be accomplished by a variety of methods known to those skilled in the art including, precipitation by ammonium sulfate or sodium sulfate followed by dialysis against saline, ion exchange chromatography, affinity or immunoaffinity chromatography as well as gel filtration, zone electrophoresis, etc. (Goding in, Monoclonal Antibodies: Principles and Practice, 2d ed., pp. 104-126, Orlando, Fla., Academic Press). It is preferable to use purified antibodies or purified fragments of the antibodies having at least a portion of an LDL binding region, including such as Fv, F(ab')$_2$, Fab fragments (Harlow and Lane, 1988, Antibody Cold Spring Harbor).

For use in binding LDL, the purified antibodies can be covalently attached, either directly or via linker, to a compound which serves as a reporter molecule to permit detection of the presence of LDL. A variety of different types of substances can serve as the reporter molecule, including but not limited to enzymes, dyes, radioactive metal and non-metal isotopes, fluorogenic compounds, fluorescent compounds, etc. Methods for preparation of antibody conjugates of the antibodies (or fragments thereof) of the invention useful for detection or monitoring are described in U.S. Pat. Nos. 4,671,958; 4,741,900 and 4,867,973.

Preferred binding epitopes may be identified from a known LDL gene sequence and its encoded amino acid sequence and used to generate antibodies to the LDL with high binding affinity. Also, identification of binding epitopes on the LDL can be used in the design and construction of preferred antibodies. For example, a DNA encoding a preferred epitope on an LDL may be recombinantly expressed and used to select an antibody which binds selectively to that epitope. The selected antibodies then are exposed to the sample under conditions sufficient to allow specific binding of the antibody to the specific binding epitope on the LDL and the amount of complex formed then detected. Specific antibody methodologies are well understood and described in the literature. A more detailed description of their preparation can be found, for example, in Practical Immunology, Butt, W. R., ed., Marcel Dekker, New York, 1984.

Reduction of Cholesterol in Serum with Modified Nanoparticles

LAMPs were used to bind LDL cholesterol in blood serum. Before the experiment, the concentration of LDL and HDL in the blood serum was determined by UV absorbance. About 500 µL of LAMP suspension in deionized water was mixed with 5 mL of serum at room temperature and stirred for 5 minutes. The change in concentration of LDL and LDH was then measured every 5 seconds. Preliminary results showed that LAMPs significantly reduce the LDL concentration without affecting HDL.

Directing the LAMPs to a Target Site

In previous experiments using the HEK 293 cell line treated with modified FITC-labeled magnetic nanoparticles, the present inventors showed that after 24 hours the cells contained high levels of LAMPs that could be directed with an external magnet. In another experiment, the present inventors injected LAMPs into mice and used a magnet to direct them to a specific site (the heart and kidneys) as shown in FIGS. 6A-6D. After 24 hours, the mice were euthanized and the heart and kidneys were removed, sectioned, and examined for LAMPs. The magnetic treatment caused an accumulation of LAMPs in the target organs much greater than that seen in heart and kidneys of mice not exposed to the magnet.

As indicated above, there is an additional pathway for lowering plasma cholesterol levels, called reverse cholesterol transport. This process is mediated by HDL which is able to absorb cholesterol from peripheral tissues and from arterial wall macrophages and carry it to the liver for conversion to bile acids and excretion.

Figure 1C:
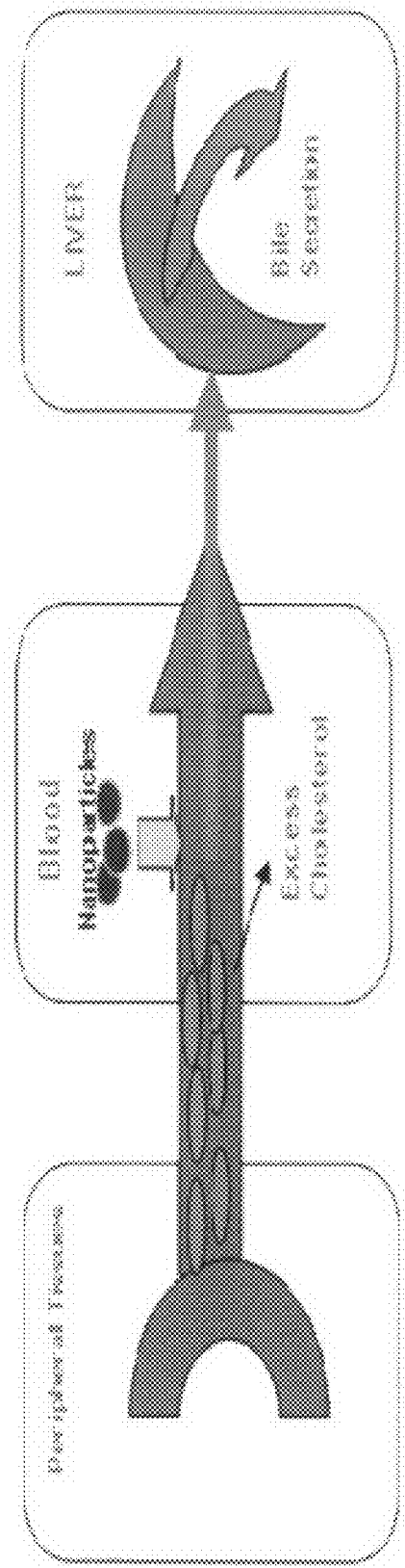
Figure 2:
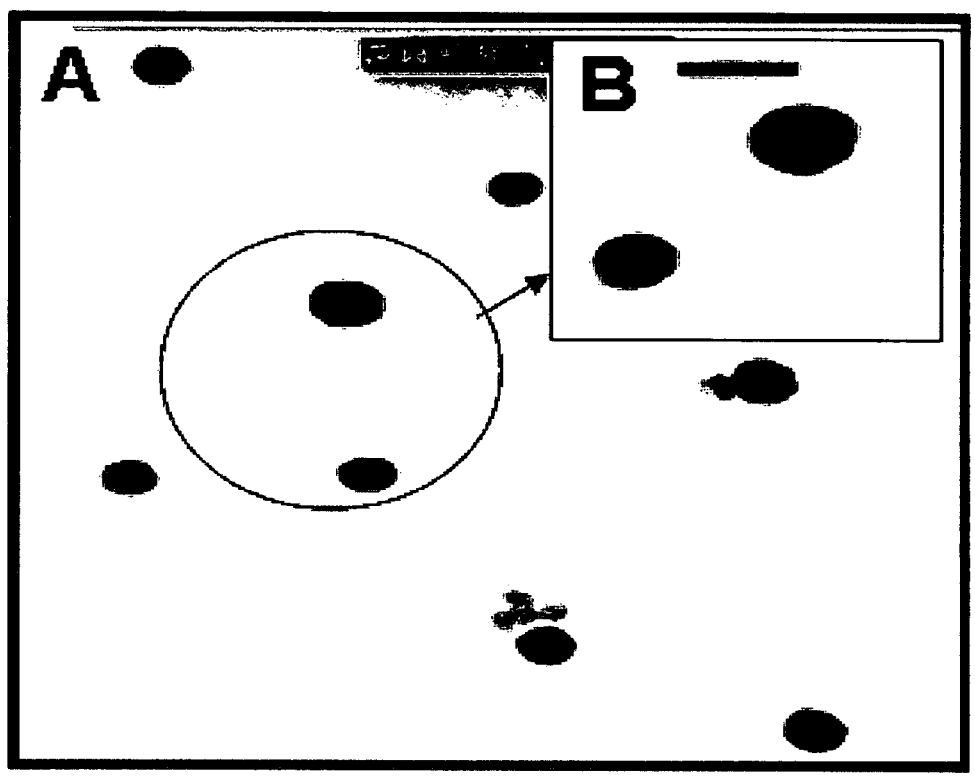
FIG. 2 shows a transmission electron micrograph (TEM) of Fe$_3$O$_4$ particles in the size range of 160 nm-220 nm. In the inset, the magnification of the nanoparticles is shown. The Fe$_2$O$_3$ nanoparticles have an average diameter of 160 nm and narrow size distributions. The colloidal suspensions of the magnetite can be oxidized by aeration to form a colloidal suspension of Fe$_2$O$_3$ particles.
Figures 3A, 3B:
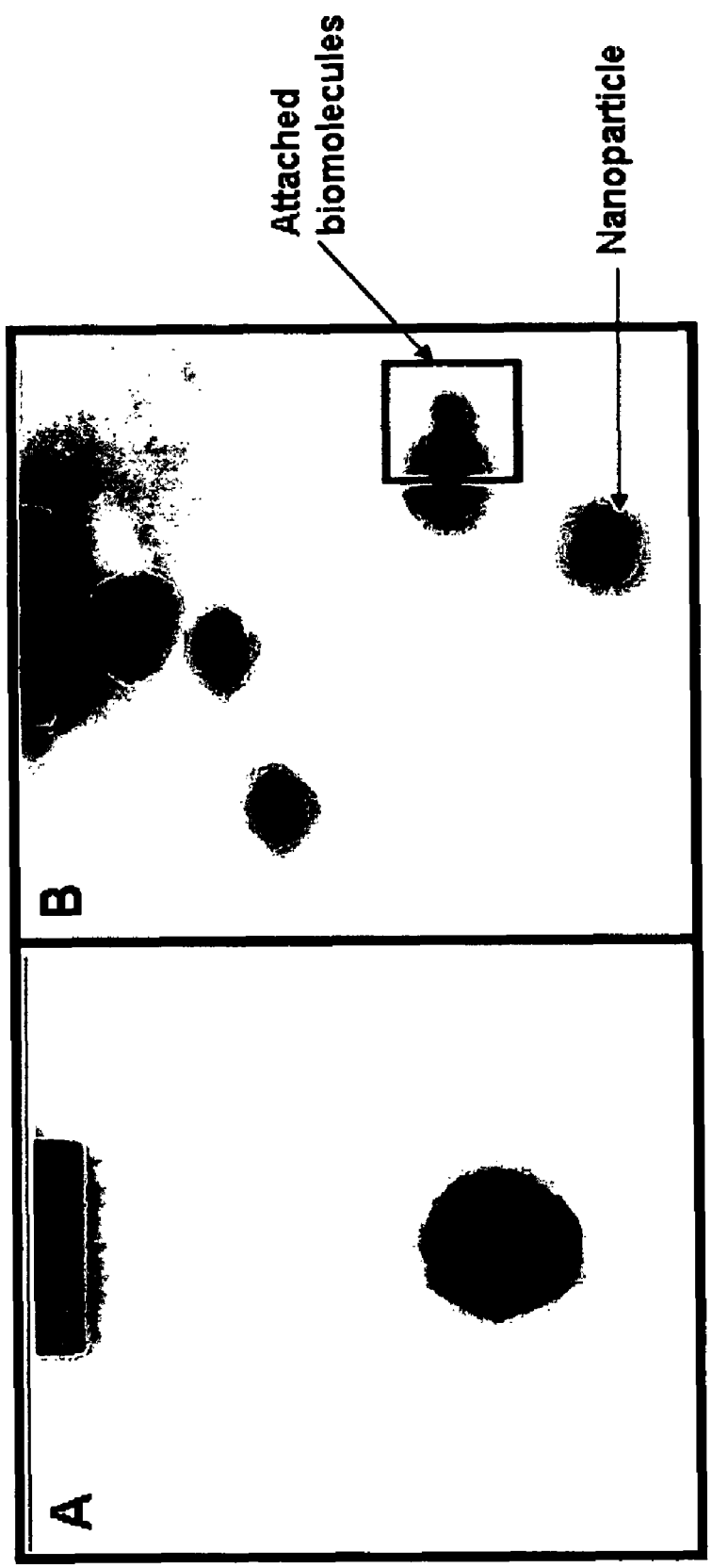
FIGS. 3A and 3B show TEMs of Fe$_3$O$_4$ Nanoparticles without modification (FIG. 3A) and after modification with Ab-7-alpha-hydroxylase and polyethylene glycol (PEG) (FIG. 3B).
Figure 4A:
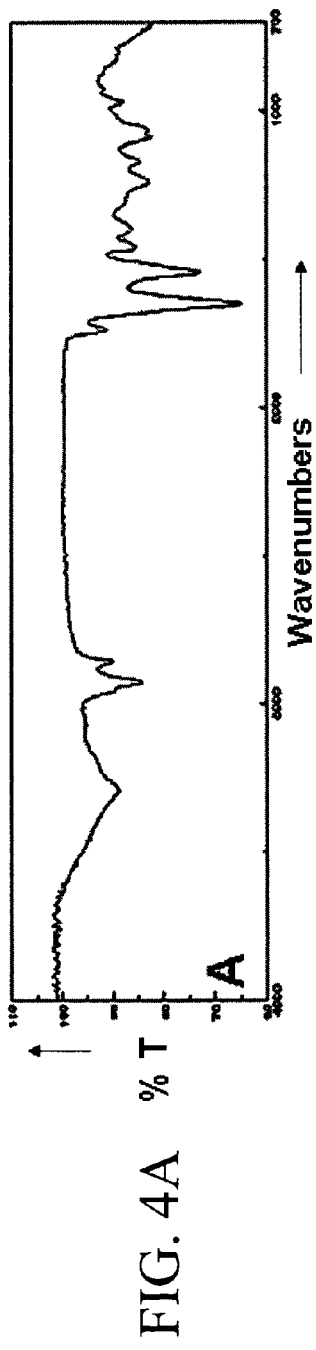
FIGS. 4A-4C show Fourier Transform Infrared Spectroscopy (FTIR) spectra of high density lipid (FIG. 4A), low density lipid (FIG. 4B), and low density lipid and antibodies attached to Fe$_2$O$_3$ nanoparticles (FIG. 4C). These results suggest that the magnetic nanoparticles are coupled with LDL antibodies.
Figure 4B:
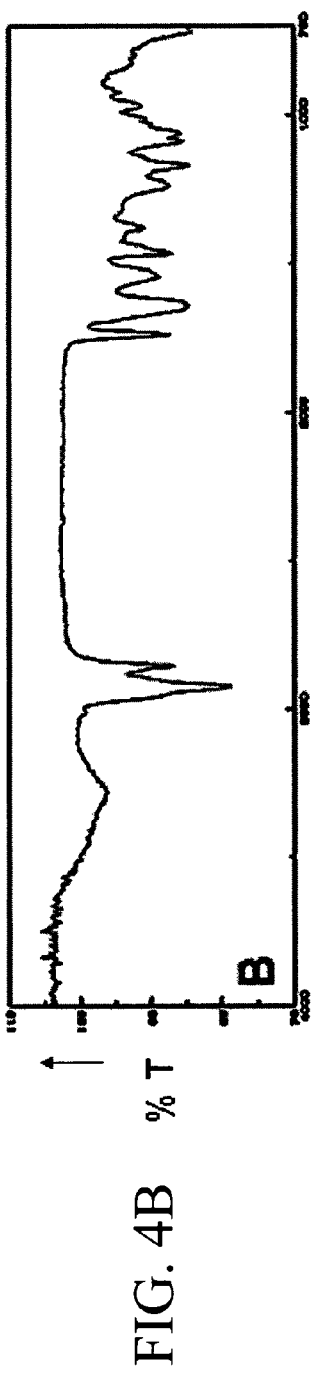
Figure 4C:
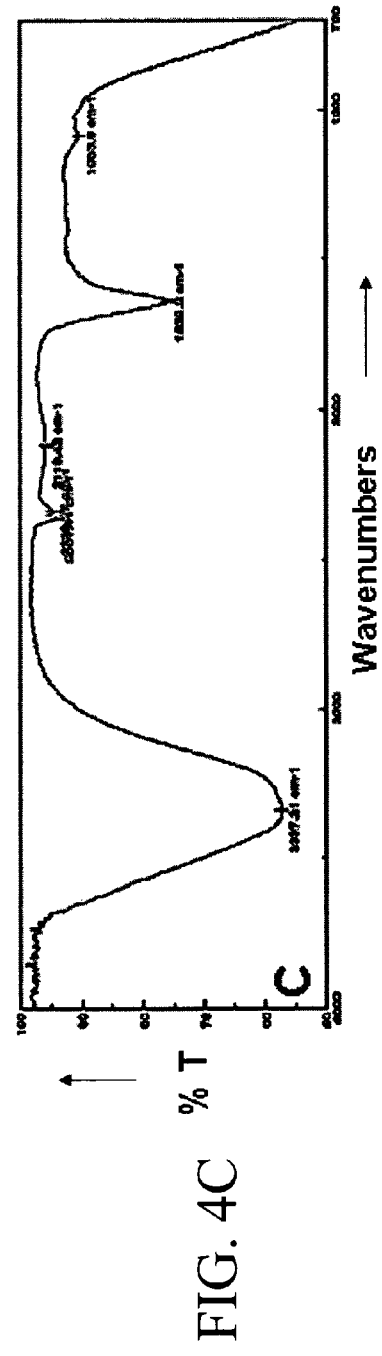
Figure 5:
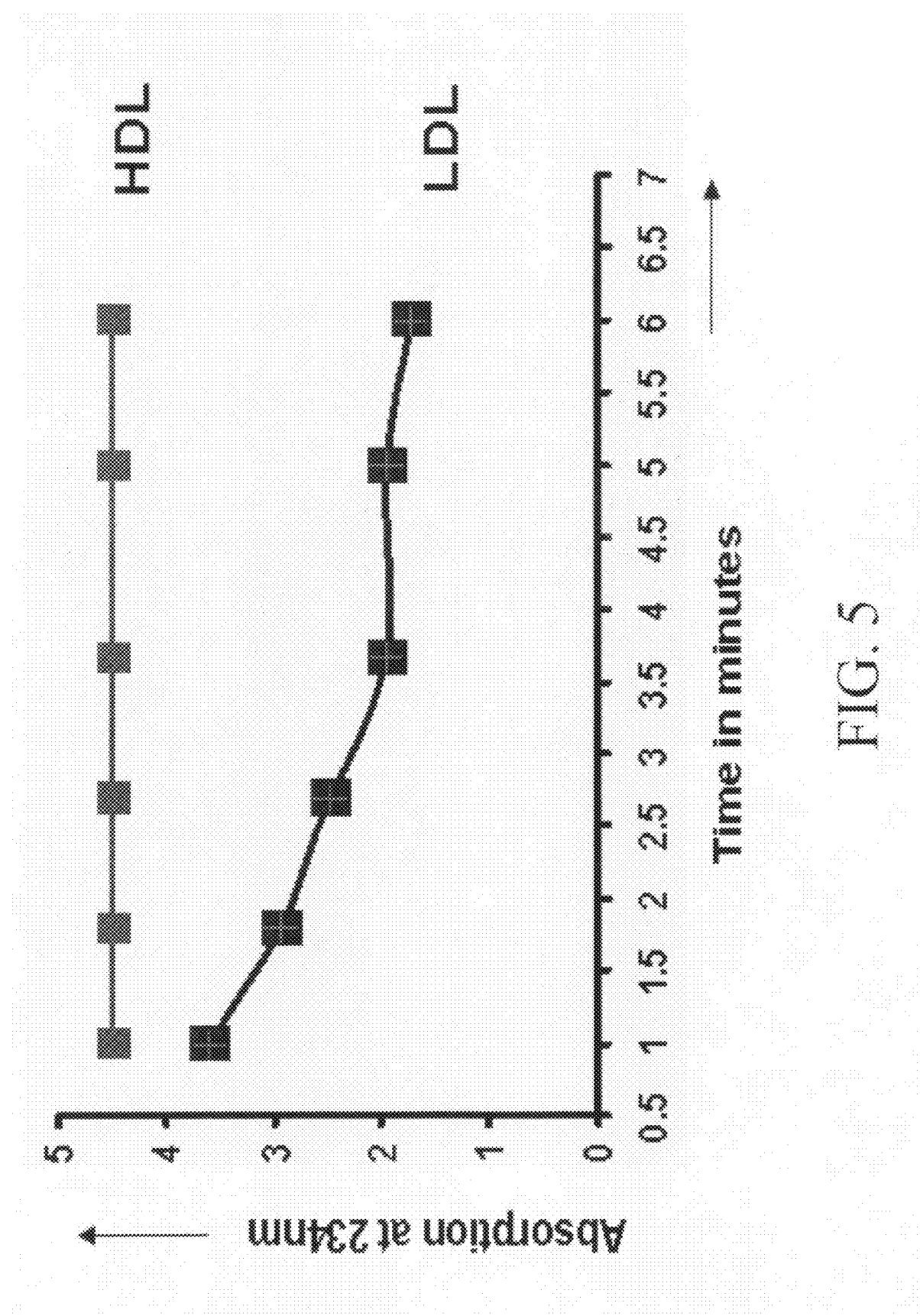
FIG. 5 is a graph demonstrating reduction in the concentration of LDL when treated with multifunctional particles and UV absorbance recorded at 234 nm.

The LAMP particles and methods of the present invention can be used to redirect LDL into bile-acid pathway. As shown in FIG. 1C, the modified LAMP particles will be injected into the circulatory system of the mouse, attach to LDL particles via the LDL antibodies. As the target organ of the magnetic particle is liver, LAMP-LDL complex will go to liver where the cholesterol will be converted to bile acids with the help of the 7-AH complexed with the particles. In alternative approach, they can be magnetically accumulated in the liver.

The vertebrate blood system contains a preponderance of capillaries; that is, the total cross-sectional area in the capillary beds greatly exceeds the cross-sectional area at any other point in the system. It is for this reason that blood flows slowly through capillary beds. Only a portion of the capillary beds are in use at any one time. Muscles in the arterial walls determine how much blood will flow through different parts of the capillary system. On the basis of these facts, the cholesterol reduction process of the invention can be optimized using a flow rate similar to the rate of flow of blood in that portion of the body for which there is a desire to reduce the cholesterol. The end products of cholesterol utilization are the bile acids, synthesized in the liver. Synthesis of bile acids is one of the predominant mechanisms for the excretion of excess cholesterol. However, the excretion of cholesterol in the form of bile acids is insufficient to compensate for an excess dietary intake of cholesterol.

Optimization of magnetic particles through selection of materials, size distribution, shape and assembly in a biopolymer matrix is important for successful use of nanoparticles as magnetic carriers for cell and molecule separation and in vivo nanoparticle targeting. The present inventors have demonstrated that magnetic nanoparticles can be targeted to tissues and organs easily using external magnets, and have shown they can also be targeted to specific cells using antibody-coated $Fe_2O_3$ particles.

According to the new guidelines released in May 2001 by the National Heart, Lung, and Blood Institute (NHLBI), most of the treatments for reducing cholesterol, including surgical procedures, are nonspecific and act on both LDL and HDL, and many cholesterol-reducing drugs cause serious side effects, such as liver failure or vitamin deficiencies. The approach of the present invention is specific for LDL and the magnitude of the reduction of cholesterol can be controlled by adjusting the dose of LAMPs.

Elevated levels of cholesterol in blood can create sticky deposits called plaque along arterial walls, and this plaque can eventually obstruct the flow of blood to the brain, heart, and other organs. Lowering cholesterol levels to 180-200 mg/dL can slow, stop, or even reverse the buildup of plaque and significantly reduces the risk of a heart attack or stroke. There are several methods available to reduce cholesterol including drugs such as the statins and surgical procedures, but none specifically target LDL and most have serious side effects. Therefore, the approach of the present invention, which utilizes reverse cholesterol transport mediated by LAMPs that are specific for LDL, offers the best combination of effectiveness and safety. However, optionally, surgical and drug interventions (such as statins) can be used in conjunction with the LAMPs and methods of the invention.

Optionally, the methods of the invention further comprise identifying a subject as one suffering from elevated cholesterol levels (e.g., elevated LDL and/or low HDL), or at risk thereof, prior to administering an effective amount of nanoparticles of the invention.

Toxicity and therapeutic efficacy of nanoparticles and nanoparticle-containing compositions can be determined by standard pharmaceutical procedures in cell cultures, other in vitro systems, or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices can be used.

Data obtained from cell culture assays and animal studies can be used in formulating a range of dosage for use in humans. The dosage of such compositions generally lies within a range of circulating concentrations that include the ED50 with little or no toxicity. The dosage can vary within this range depending upon the dosage form employed and the route of administration utilized. For any composition used in the method of the invention, the therapeutically effective dose can be estimated initially from cell culture or other in vitro assays. A dose can be formulated in animal models to achieve a circulating plasma concentration range that includes the IC50 (i.e., the concentration of the test composition which achieves a half-maximal inhibition of symptoms) as determined in cell culture or other in vitro systems. Such information can be used to more accurately determine useful doses in humans. Levels in plasma can be measured, for example, by high performance liquid chromatography.

The nanoparticles and nanoparticle-containing compositions of the invention can be administered on any appropriate schedule, e.g., from one or more times per day to one or more times per week; including once every other day, for any number of days or weeks, e.g., 1 day, 2 days, 3 days, 4 days, 5 days, 6 days, 1 week, 10 days, 2 weeks, 3 weeks, 4 weeks, 5 weeks, 6 weeks, 7 weeks, 8 weeks, 2 months, 3 months, 6 months, or more, or any variation thereon. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of nanoparticles can include a single treatment or can include a series of treatments.

Mammalian species that benefit from the disclosed methods include, but are not limited to, primates, such as apes, chimpanzees, orangutans, humans, monkeys; domesticated animals (e.g., pets) such as dogs, cats, and wild or exotic animals. As used herein, the terms "subject", "host", and "patient" are used interchangeably and intended to include such human and non-human mammalian species.

The terms "comprising", "consisting of" and "consisting essentially of" are defined according to their standard meaning. The terms may be substituted for one another throughout the instant application in order to attach the specific meaning associated with each term.

The terms "isolated" or "biologically pure" refer to material that is substantially or essentially free from components which normally accompany the material as it is found in its native state.

As used in this specification, the singular forms "a", "an", and "the" include plural reference unless the context clearly dictates otherwise. Thus, for example, a reference to "a nanoparticle" includes more than one such nanoparticle. A reference to "an antibody" includes more than one such antibody. A reference to "a molecule" includes more than one such molecule, and so forth.

The practice of the present invention can employ, unless otherwise indicated, conventional techniques of molecular biology, microbiology, recombinant DNA technology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

Following are examples that illustrate materials, methods, and procedures for practicing the invention. The examples are illustrative and should not be construed as limiting.

EXAMPLE 1

Preparation of Magnetic $Fe_2O_3$ Nanoparticles

A. Materials and Methods

Material: Iron (II) chloride, Iron (III) chloride 97%, deionized water with (resistance 17.8 MΩ) and necessary glass apparatus.

Method: In preparing homogeneous nanoparticles it is preferable to perform the reaction under basic aqueous conditions without surfactants using a molar ratio of Fe (II):Fe (III)=1:2. Deionized water (resistance 17.8 MΩ) was used to suspend the components with vigorous stirring. The resulting aqueous suspension was precipitated by the spray method and the resulting magnetic particles washed with deionized water to remove unreacted components (Shang, H et al. *Langmuir*, 2006 Mar. 14, 22(6):2516-2522; Gomez-Lopera, S A et al. *Langmuir*, 2006 Mar. 14, 22(6):2816-2821; Fuentes, M et al. *Biosens Bioelectron*, 2005, 20(7):1380-1387).

B. Results

The preparation of magnetic nanoparticles is performed in aqueous medium and obtain particles of specific size (60-160 with narrow distribution).

EXAMPLE 2

Attachment of LDL Antibodies and 7-alpha Hydroxylase to Magnetic Nanoparticles

A. Materials and Methods

Material: $Fe_2O_3$ nanoparticles (60-160 nm with narrow distribution), LDL antibodies, β7 hydroxylase and NADH Method: A solution of LDL antibodies in deionized water was mixed with 0.5 mL of carbodiimide solution and added to a colloidal suspension of magnetic nanoparticles. The solution was left to stand for 15 minutes to allow hydrolysis of the surface groups and formation of vitreophilic nanoparticles. The functionalized suspension was stirred vigorously and allowed to stand for at least 24 hours to produce LDLAb- Fe$_2$O$_3$ (LAMP) nanoparticles. The same procedure was followed for adsorbing 7-alpha hydroxylase to the LAMPs (Lee, H Y et al. *J Nanosci Nanotechnol,* 2002, 2(6):613-615; Chu, Y et al. *J Phys Chem B Condens Matter Mater Surf Interfaces Biophys.,* 2006 Feb. 23, 110(7):3135-3139). The LAMPs were then washed with deionized water to remove any excess components and added to a mixture of ethanol and NH$_4$OH (25%) with vigorous stirring. The suspension was then gently stirred for 2 hours at room temperature, and water evaporated under vacuum. The average diameter of the LAMPs was determined by transmission electron microscopy (TEM). The coupling of the antibodies and enzyme were confirmed by Fourier transform infrared spectroscopy (FTIR). FTIR measurements also showed that LAMPs specifically bind LDL in solutions containing both LDL and HDL (Hernando, A et al. *Scientific World Journal,* 2005, 5:972-1001, Review; Osaka, T et al. *Anal Bioanal Chem.,* 2006 February, 384(3):593-600, Epub Jan. 4, 2006; Pouliquen, D et al. *Magn Reson Imaging,* 1993, 11(2):219-228).

B Results: In the next step LDL antibodies, 7-alpha hydroxylase and the enzyme cofactor NADH are adsorbed to the particles and the resulting LAMPs are tested in vitro.

EXAMPLE 3

Reduction of Cholesterol in Serum with Modified Nanoparticles

A. Materials and Methods

Material: Human serum, modified iron oxide nanoparticles with LDL antibodies and enzymes and biomolecules as discussed in Examples 1 and 2.

Methods: LAMPS were used to bind LDL cholesterol in blood serum. Before the experiment, the concentration of LDL and HDL in the blood serum was determined by UV absorbance. About 500 μL of LAMP suspension in deionized water was mixed with 5 mL of serum at room temperature and stirred for 5 minutes. The change in concentration of LDL and LDH was then measured every 5 seconds. Preliminary results showed that LAMPs significantly reduce the LDL concentration without affecting HDL.

Results: LAMPs are mixed with a blood serum sample, stirred, and the relative levels of LDL and HDL determined spectrophotometrically. The LAMPs are able to specifically remove LDL from serum.

EXAMPLE 4

Directing the LAMPs to a Specific Site

A. Materials and Methods

Materials:
  Animals. Six-week old female BALB/c mice from Jackson laboratory (Bar Harbor, Me.) were maintained in pathogen-free conditions in accordance with animal research committee regulations. Magnets and modified iron oxide nanoparticles.

Methods: In previous experiments using the HEK 293 cell line treated with modified FITC-labeled magnetic nanoparticles, the present inventors showed that after 24 hours the cells contained high levels of LAMPs that could be directed with an external magnet. In another experiment, LAMPs were injected into mice and a magnet was used to direct them to a specific site (the heart and kidneys) as shown in FIGS. 6A-6D. After 24 hours, the mice were euthanized and the heart and kidneys were removed, sectioned and examined for LAMPs. The magnetic treatment caused an accumulation of LAMPs in the target organs much greater than that seen in heart and kidneys of mice not exposed to the magnet.

Results: For in vivo determinations, FITC-labeled magnetic particles are injected into mice and directed to the heart or kidney using a magnet. The organs exposed to the magnetic field show significantly elevated levels of LAMPs.

EXAMPLE 5

Preparation of Chitosan Nanoparticles

Methods: Chitosan nanoparticles were prepared by ionic gelation of CS with TPP (tripolyphosphate) anions. In this approach, chitosan was dissolved in acetic aqueous solution at various concentrations. In the next step, under magnetic stirring at room temperature, 4 mL of sodium tripolyphosphate (TPP) aqueous solution with various concentrations was added into 10 mL of chitosan solution, respectively. Three kinds of phenomena were observed: solution, aggregates and an opalescent suspension. The zone of opalescent suspension was formed due to nanoparticle formation. Further, these particles were coated with PEG by incorporating 4 mL of TPP solution into 10 mL chitosan solution containing various concentrations of PEG.

Figure 7A:
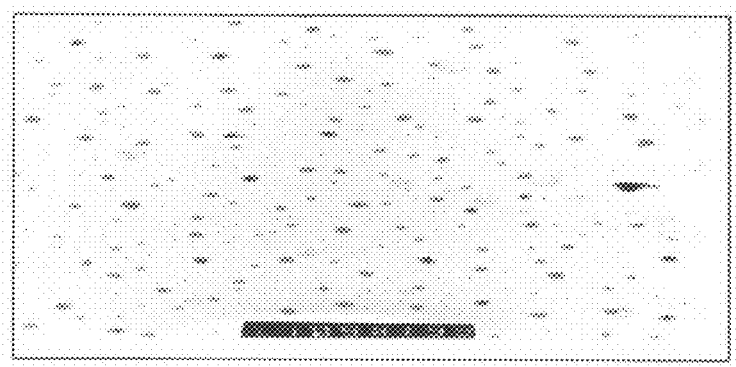
FIGS. 7A and 7B show TEMs of nanoparticles of the invention.
Figure 7B:
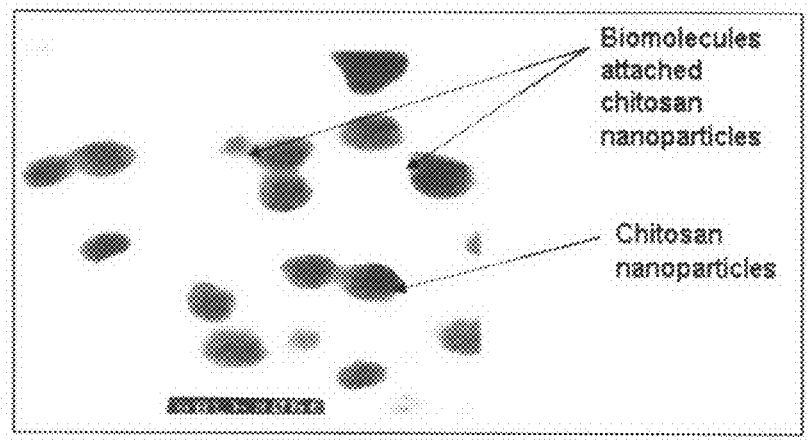

Results: Results show the TEM of chitosan-PEG nanoparticles with uniform size in the range of 60-80 nM (FIG. 7A) and a TEM of chitosan nanoparticles modified with LDL antibodies and 7-alpha hydroxylase (FIG. 7B).

EXAMPLE 6

Attachment of LDL Antibodies and 7-alpha Hydroxylase to Chotosan Nanoparticles

Methods:
  A. Preparation of Water soluble chitosan. Chitosan was dissolved in aqueous acetic acid. Methanol was added and the solution mixed. Then, a methanol solution of acetic anhydride was poured in while the solution was well stirred. After standing at room temperature for 2 hours, the solution was poured into methanolic ammonia and the precipitate filtered off, washed well with aqueous methanol, then methanol, and dried under vacuum. The product had 58% N-acetylation and was water-soluble.
  B. Coupling the LDL antibodies with Chitosan nanoparticles. A solution of LDL antibodies in deionized water was mixed with 0.5 mL of carbodiimide solution and added to a colloidal suspension of chitosan nanoparticles. The solution was left to stand for 15 minutes to allow hydrolysis of the surface groups and formation of vitreophilic nanoparticles. The functionalized suspension was stirred vigorously and allowed to stand for at least 24 hours to produce LDLAb-chitosan nanoparticles. The same procedure was followed for adsorbing 7-alpha hydroxylase to the chitosan nanoparticles (Willner, I. and Katz, E. *Langmuir,* 2006 Feb. 14, 22(4):1409-19; Alexiou, C. et al. *Eur Biophys J.,* 2006 Jan. 31, 1-5).
  C. Purification and characterization of the modified chitosan nanoparticles. The modified chitosan nanoparticles were then washed with deionized water to remove any excess components and water evaporated under vacuum with mild heating at about 25° C. The average diameter of the chitosan nanoparticles was determined by transmission electron microscopy (TEM) and found to be in the range of 60-80 nM. The coupling of the antibodies and enzyme were confirmed by Fourier transform infrared spectroscopy (FTIR). FTIR measurements also showed that LAMPs specifically bind LDL in solutions containing both LDL and HDL (Kuhn, S. J. et al. *Ann Biomed Eng.*, 2006 January, 34(1):51-8, Epub 2006 Feb. 14; Thunemann, A. F. et al. *Langmuir,* 2006 Feb. 28, 22(5):2351-7; Bruckl, H. et al. *IEE Proc Nanobiotechnol.,* 2005 February, 152(1):41-6; Koh, I. et al. *J Phys Chem B Condens Matter Mater Surf Interfaces Biophys.,* 2006 Feb. 2, 110(4):1553-8).

Results: The results of TEM analysis following conjugation of chitosan nanoparticles with LDL antibodies and 7-alpha hydroxylase are shown in FIG. 7B.

EXAMPLE 7

Reduction of Cholesterol in Serum with Modified Chitosan Nanoparticles

Methods. Modified chitosan naoparticles are intended to bind with LDL cholesterol in blood serum. To test this hypothesis, the present inventors introduced a fixed amount of modified chitosan into a tube containing 5 mL of blood serum with known concentrations of HDL and LDL. Before the experiment, the concentration of LDL and HDL in the blood serum was determined by UV absorbance. About 500 μL of modified chitosan was suspended into deionized water. Next, a modified chitosan nanoparticle solution was mixed with 5 mL of serum at room temperature and stirred for 5 minutes. The change in concentration of LDL and LDH was then measured every 30 seconds.

Figure 8A:
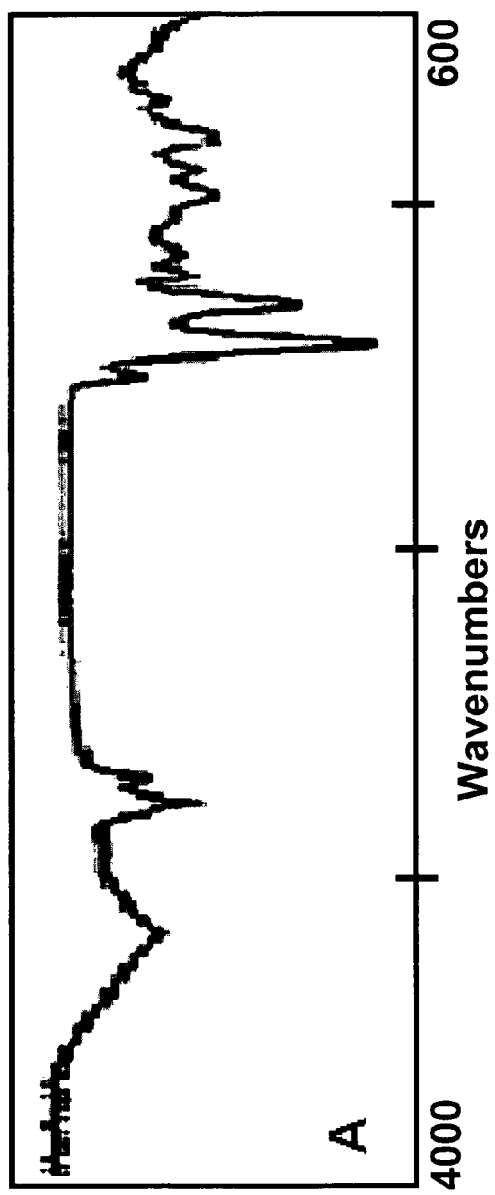
FIGS. 8A and 8B show FTIR spectra of chitosan nanoparticles before modification (FIG. 8A), and after modification with LDL antibodies (FIG. 8B). These results suggest that the chitosan nanoparticles are coupled with LDL antibodies.
Figure 8B:
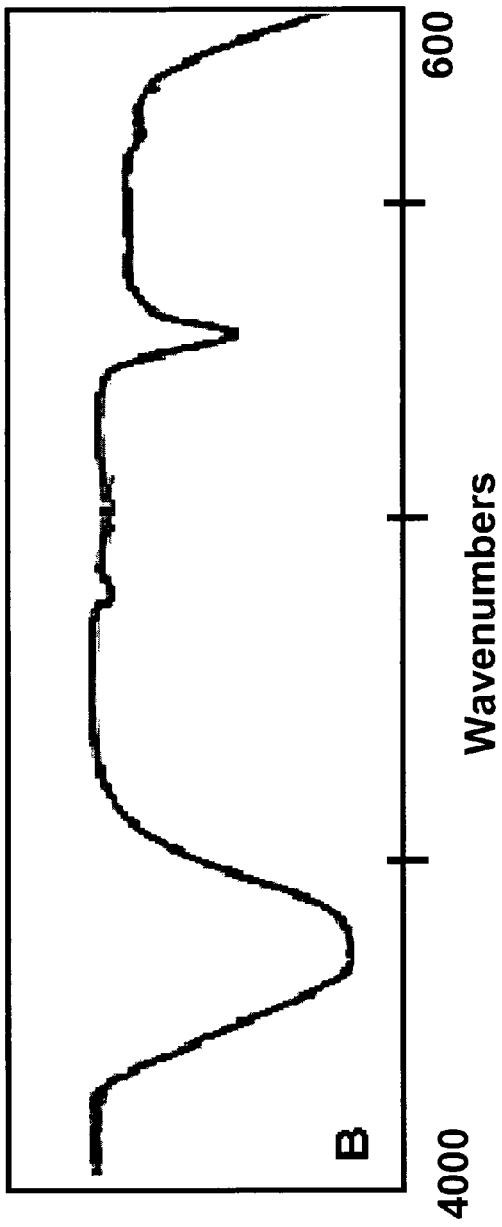
Figure 9:
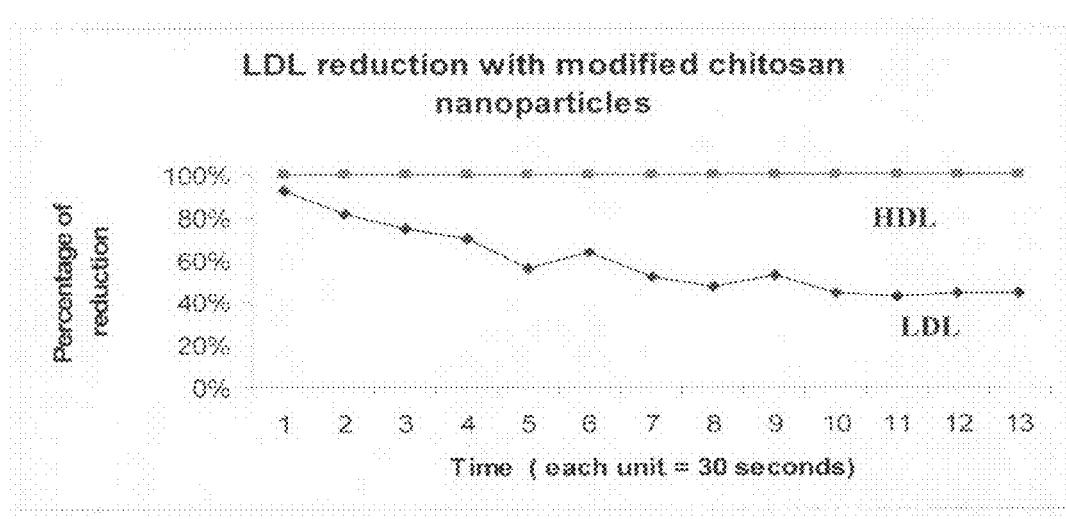
FIG. 9 shows a reduction in the concentration of LDL in blood serum in vitro when treated with modified chitosan nanoparticles. UV absorbance was recorded at 234 nm.

Results: Results showed that modified chitosan nanoparticles significantly reduced the LDL concentration without affecting HDL. The results are shown in FIG. 9 and indicate reduction of DL cholesterol compared to control (FIGS. 8A-8B and FIG. 9).

All patents, patent applications, provisional applications, and publications referred to or cited herein, supra or infra, are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A nanoparticle comprising:
    a. a core comprising a metal, a polymer, or a combination thereof;
    b. a low-density lipoprotein (LDL) binding agent attached to said core;
    c. 7-α hydroxylase or an enzymatically active fragment thereof attached to said core; and
    d. nicotinamide adenine dinucleotide (NADH) attached to said core.

2. The nanoparticle of claim 1, wherein said core comprises $Fe_3O_4$ and/or $Fe_2O_3$.

3. The nanoparticle of claim 1, wherein said core comprises at least one metal selected from the group consisting of iron, cobalt, nickel, aluminum, and cobalt/silica.

4. The nanoparticle of claim 1, wherein said core comprises chitosan.

5. The nanoparticle of claim 1, wherein said LDL binding agent is an antibody or antibody fragment that specifically binds to LDL.

6. The nanoparticle of claim 1, wherein said core further comprises a polymer coating.

7. The nanoparticle of claim 1, further comprising a reporter molecule.

8. The nanoparticle of claim 1, wherein the nanoparticle comprises 7-α hydroxylase attached to said core.

9. The nanoparticle of claim 6, wherein said polymer is polyethylene glycol (PEG).

10. The nanoparticle of claim 9, wherein said core comprises chitosan coated with PEG.

* * * * *